(12) United States Patent
Gilad et al.

(10) Patent No.: US 9,113,845 B2
(45) Date of Patent: Aug. 25, 2015

(54) DEVICE AND METHOD FOR ASSEMBLING IN VIVO SENSING DEVICES

(75) Inventors: Zvika Gilad, Haifa (IL); Chen Mann, Kibbutz Merhavia (IL); Semion Khait, Tiberias (IL)

(73) Assignee: GIVEN IMAGING LTD., Yoqneam (IL)

( * ) Notice: Subject to any disclaimer, the term of this patent is extended or adjusted under 35 U.S.C. 154(b) by 1030 days.

(21) Appl. No.: 12/350,372

(22) Filed: Jan. 8, 2009

(65) Prior Publication Data

US 2010/0174141 A1    Jul. 8, 2010

(51) Int. Cl.
| | |
|---|---|
| *A61B 1/00* | (2006.01) |
| *A61B 5/00* | (2006.01) |
| *H05K 1/18* | (2006.01) |
| *A61B 1/04* | (2006.01) |
| *H05K 3/46* | (2006.01) |

(52) U.S. Cl.
CPC ............ *A61B 5/6861* (2013.01); *A61B 1/0011* (2013.01); *A61B 1/041* (2013.01); *H05K 1/189* (2013.01); *H05K 3/4691* (2013.01); *H05K 2201/042* (2013.01); *H05K 2201/09027* (2013.01); *Y10T 29/5313* (2015.01)

(58) Field of Classification Search
CPC ...................................................... H05K 5/00
USPC ................... 600/103, 117, 118, 160, 178, 101
See application file for complete search history.

(56) References Cited

U.S. PATENT DOCUMENTS

| | | | | |
|---|---|---|---|---|
| 4,834,659 | A | * | 5/1989 | Mang et al. ...................... 439/55 |
| 5,252,815 | A | * | 10/1993 | Pernet ............................ 235/441 |
| 5,738,012 | A | * | 4/1998 | Metrope .................... 101/415.1 |
| 5,995,373 | A | * | 11/1999 | Nagai ............................ 361/755 |
| 6,083,037 | A | * | 7/2000 | Gunther et al. ................ 439/443 |
| 7,597,259 | B2 | * | 10/2009 | Nishikawa et al. ............ 235/441 |
| 2002/0001979 | A1 | * | 1/2002 | Akram et al. .................... 439/32 |
| 2004/0171914 | A1 | | 9/2004 | Dov |
| 2005/0138772 | A1 | * | 6/2005 | Park ................................ 16/330 |
| 2006/0264704 | A1 | * | 11/2006 | Fujimori et al. ............... 600/101 |
| 2007/0118012 | A1 | * | 5/2007 | Gilad ............................ 600/109 |
| 2007/0229656 | A1 | * | 10/2007 | Khait et al. ...................... 348/77 |
| 2007/0258236 | A1 | * | 11/2007 | Miller ............................ 362/205 |

FOREIGN PATENT DOCUMENTS

| | | | | | |
|---|---|---|---|---|---|
| JP | | 2001091860 A | * | 4/2001 | ............. G02B 23/24 |
| WO | WO 2006/070360 | | | 7/2006 | |

OTHER PUBLICATIONS

International Search Report, issued May 17, 2010, for International Patent Application No. PCT/IL10/00012.

* cited by examiner

*Primary Examiner* — Anhtuan T Nguyen
*Assistant Examiner* — Rynae Boler
(74) *Attorney, Agent, or Firm* — Pearl Cohen Zedek Latzer Baratz LLP

(57) ABSTRACT

A sleeve for simple assembly of in-vivo devices, such as endoscopy capsules, is provided. The sleeve comprises grippers and leaf springs at either end to hold the rigid portions of a rigid-flex PCB (printed circuit board) in a folded configuration before the PCB is inserted into an in-vivo device's housing. A method of assembly of the rigid-flex PCB into the sleeve is provided.

21 Claims, 9 Drawing Sheets

DEVICE AND METHOD FOR ASSEMBLING IN VIVO SENSING DEVICES

FIELD OF THE INVENTION

The present invention relates to the field of assembly of in-vivo devices. More specifically the present invention relates to a device and method for assembling an in-vivo sensing device for capsule endoscopy.

BACKGROUND OF THE INVENTION

Many devices, specifically devices that are intended to be inserted in-vivo, may need to maintain a small volume so as to enable free passage through in-vivo ducts. Many in-vivo devices, such as in-vivo endoscopy capsules, contain electronic and electrical components, e.g., image sensors, illumination sources, transmitters, antennas, etc. Typically, such components are supported by and are electrically connected to a printed circuit board (PCB). The PCB on which electronic components are mounted is typically a rigid printed circuit board. In-vivo endoscopy capsules normally comprise numerous electronic components, such that the electronic components are divided between at least two rigid portions. Such rigid portions are typically connected by a flexible portion, i.e., the PCB used in in-vivo devices is a "rigid-flex" PCB.

The rigid-flex PCB is inserted into a device with a predetermined low volume that is compatible with the known size and diameter of in-vivo lumens and ducts into which it is inserted. For example, a swallowable capsule should maintain a low volume compatible with the smallest diameter of the gastrointestinal (GI) tract, such that the capsule can freely pass through the GI tract. In order for the device to maintain a low volume, the rigid-flex PCB needs to be kept within the device in a compact configuration.

During assembly, all the electronic and electrical components are mounted on the rigid-flex PCB prior to the PCB being folded into a compact configuration. Rigid-flex PCBs which are intended to be inserted in endoscopy capsules according to embodiments of the present invention may be similar to embodiments described in International Patent Application Number PCT/IL2005/001380, entitled "In-Vivo Sensing Device With A Circuit Board Having Rigid Sections And Flexible Sections", filed on Dec. 27, 2005, published on Jul. 6, 2006 as International Patent Application Publication Number WO 2006/070360 and/or in U.S. patent application Ser. No. 10/481,126, entitled "In-Vivo Sensing Device With A Circuit Board Having Rigid Sections And Flexible Sections", filed on Dec. 18, 2003, published on Sep. 2, 2004 as United States Patent Application Publication Number 2004/0171914, which describes a rigid-flex PCB that is folded and held in its folded configuration through mini-springs or spacers between one rigid portion and another. In this embodiment, the springs/spacers may hold the PCB in its folded configuration by gluing the ends of the rigid portions of the PCB to the ends of the springs/spacers, all of which are hereby incorporated by reference.

However, glue may be difficult to use during assembly, and glue may drip and/or may spread to areas where it is not needed, as well as reach areas where it may cause damage, e.g., cause a cut-off between electrical components on the PCB. During mass production, especially during production of devices of a small scale, e.g., swallowable endoscopy capsules, the use of glue complicates the assembly process, since it is difficult to control the amount of glue used and its polymerization.

There is, therefore, a need for a more simple way of assembly and folding of a rigid-flex PCB into an in-vivo device, while maintaining it in its folded position.

Furthermore, in an event of a short circuit in one of the electrical circuits in an in-vivo device, the batteries inside may over-heat. In order to prevent over-heating of the in-vivo device's housing which may lead to undesirable heating of tissue surrounding the device, there is a need for a mechanism that may distant the batteries from the in-vivo device's housing.

SUMMARY OF THE INVENTION

Embodiments of the present invention provide a device and method for easy and simple assembly and folding of a PCB into an in-vivo device.

In some embodiments of the present invention, an in-vivo device may comprise a sleeve with grippers and leaf springs instead of glue. Such a sleeve may be beneficial in simplifying the assembly process of in-vivo devices. When using a sleeve with grippers and leaf springs instead of springs/spacers connected by glue, as will be described in the invention below, the assembly process of in-vivo devices may be less time-consuming and may acquire less expertise such that it is more cost-effective.

In addition, a sleeve may serve as a barrier between the device's housing and batteries placed inside the device and so may prevent over-heating of the device's housing in the event of a short-circuit which inevitably causes over-heating of the batteries.

According to some embodiments, there is provided a sleeve configured for holding a circuit board in a folded configuration, said circuit board comprising a first rigid portion and a second rigid portion connected by a flexible portion. According to some embodiments, the sleeve may comprise a first end comprising a first gripper and at least two leaf springs, and a second end comprising a second gripper. In some embodiments, the first gripper and the at least two leaf springs are for holding the first rigid portion in between the first gripper and the two leaf springs. In some embodiments, the second gripper is for holding the second rigid portion. In some embodiments, the sleeve may comprise space for inserting at least one battery between the first and the second rigid portions.

In some embodiments, the sleeve may be manufactured from a material selected from: Acetal, ABS, Polycarbonate, and Polyimide. In some embodiments, the sleeve may be inserted into a swallowable capsule's housing. According to some embodiments, the sleeve may comprise a longitudinal opening through which the flexible portion is passed along. In some embodiments, the opening may be for providing space for the flexible portion between the sleeve and the capsule's housing.

According to some embodiments, a method of assembling an in vivo device is provided. In some embodiments, the method may comprise the step of providing a sleeve with two open ends, wherein a first sleeve end comprises a first gripper and at least two leaf springs and a second sleeve end comprises a second gripper. The method may further comprise the steps of providing a circuit board having a first rigid portion and a second rigid portion connected by a flexible portion, and pushing the first rigid portion into the first gripper, such that the first rigid portion is placed between the first gripper and the two leaf springs.

In some embodiments, the method may comprise the step of folding the circuit board while passing the flexible portion between the first and second sleeve ends and pushing the second rigid portion into the second gripper. In some embodiments, the method may comprise the step of inserting at least one battery into the sleeve prior to folding the circuit board.

According to some embodiments, the method may further comprise the steps of inserting the sleeve into an in-vivo device's housing, placing an optical dome on one side of the in-vivo device's housing, and placing a cover on another side of the in-vivo device's housing. According to some embodiments, the cover placed on the in-vivo device's housing may be an optical dome. In some embodiments, the in-vivo device may be a swallowable capsule.

BRIEF DESCRIPTION OF THE DRAWINGS

The present invention will be understood and appreciated more fully from the following detailed description taken in conjunction with the appended drawings in which.

Figure 1:
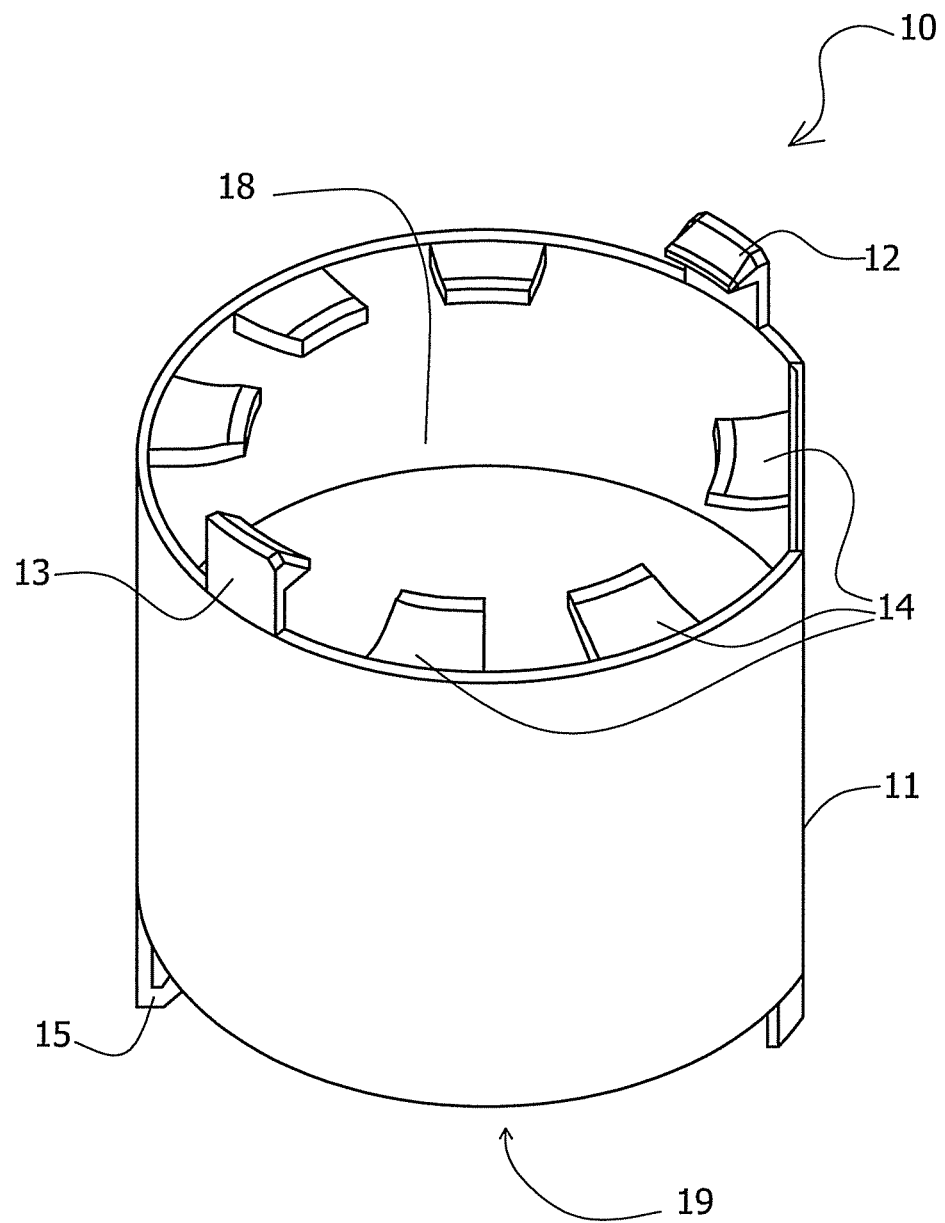
FIG. 1 is a schematic illustration of a sleeve for folding a rigid-flex PCB in accordance with one embodiment of the invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Reference is now made to FIG. 1, which provides a schematic illustration of a sleeve for folding a rigid-flex PCB (Printed circuit board) in accordance with one embodiment of the invention. According to an embodiment of the invention, as described in FIG. 1, there is provided a sleeve 10, which comprises a sleeve body 11 and two open ends 18, 19. Sleeve body 11 may be cylindrical, as shown in FIG. 1, but may also have other shapes that fit conveniently and efficiently within an in-vivo device. In preferred embodiments, sleeve body 11 is open at both ends. In some embodiments, there may be at least one gripper 12 on one open end 18 of the sleeve body 11 and at least one gripper 15 on the other open end 19 of the sleeve body 11. In some embodiments there may be one or more additional grippers on either end, such as gripper 13. Gripper 12 and/or gripper 13 are for retaining a rigid portion of the rigid-flex PCB perpendicularly to the axial direction of the sleeve 11, against the upper rim of the sleeve 11 and against leaf springs 14 to be further described. Gripper 15 is to retain a rigid portion of the rigid-flex PCB perpendicularly to the axial direction of the sleeve 11 against the lower rim of the sleeve 11.

According to some embodiments, sleeve 10 may further comprise leaf springs 14 for supporting a rigid portion of the PCB across the opening 18 of the sleeve 11. Leaf springs 14 have a planar shape that is oriented generally perpendicular to the axial direction of the sleeve 11, and leaf springs 14 extend radially inward into opening 18 from the outside rim of sleeve 11. In some embodiments, leaf springs 14 may be on either end of the sleeve body 11, or on both ends of the sleeve body 11. The quantity of leaf springs 14 may vary according to design requirements, e.g., the size of the rigid portions of a rigid-flex PCB which may be supported by leaf springs 14. For example, the larger the diameter of the rigid portion, the larger the quantity of leaf springs which may be used. In other embodiments, the number of leaf springs may be the same for any rigid portion's diameter, although the leaf springs may have larger dimensions in order to provide the rigid portion the support needed. Namely, in order to provide adequate support to rigid portions with varying dimensions, the leaf springs may either vary in size or quantity. In any case, there is typically more than one leaf spring present on either end 18/19 of sleeve 11.

According to some embodiments, leaf springs 14 are positioned at the end of the sleeve body 11, such that one rigid portion of the rigid-flex PCB may be inserted and held securely between gripper(s) 12 (and 13) and leaf springs 14. In some embodiments, leaf springs 14 may serve as support for the rigid-flex PCB to prevent the rigid portion of the PCB from entering into the interior of sleeve 11. The rigid portion of the PCB may be pushed or snapped under grippers 12 and 13 while being supported by leaf springs 14. In some embodiments, leaf springs 14 may not act as springs but may only provide mechanical support for a rigid portion of the PCB, namely by resting onto said leaf springs 14 the side of the rigid portion opposite the side of rigid portion that grippers 12 and 13 contact, such to ensure that the rigid portion is properly held at the opening 18/19 of the sleeve body 11. In other embodiments, leaf springs 14 may serve as actual springs, i.e., leaf springs 14 may apply force on the side of the rigid portion opposite the side of the grippers, pushing it towards the underside of the overhanging portion of gripper 12 (and 13). Leaf springs 14 may push one of the rigid portions of the rigid-flex PCB against grippers 12 and 13 so as to ensure a tight and firm hold of that rigid portion of the PCB within the sleeve 10.

In some embodiments, due to the vagaries of mass production, the rigid portion of the rigid-flex PCB may have various widths since the tolerance during production is quite high. During mass production, the rigid portion of the PCB may be designed to have a final width of typically 0.70 mm but may also have a tolerance of about ±0.1 mm, which is of the same scope as the final width. Such a high tolerance may lead to a large variance in the width of the rigid portion. In order to ensure that the rigid portion of the PCB will stay within the gripper 12 (and 13) so as to ensure that the rigid-flex PCB is held in a folded configuration, the sleeve 10 includes leaf springs 14. In some embodiments, leaf springs 14 are designed to push the rigid PCB portion against the underside of the overhanging portion of gripper 12 (and 13). Leaf springs 14 overcome the large variance of the rigid portions' widths by pushing the rigid portion against the underside of the overhanging portion of gripper 12 (and 13). This secures the rigid portion of the PCB in between the grippers 12 and 13 and leaf springs 14.

According to some embodiments, sleeve 10 may be made of any thermoplastic polymer such as Acetal, ABS, Polycarbonate, and Polyimide. Other materials may be used.

In some embodiments, the dimensions of the sleeve 10 may be for example, 10 mm in diameter, 10 mm in height and 0.3 mm in wall thickness. These dimensions are suitable for a sleeve intended to be inserted into a housing of the swallowable endoscopy capsule PillCam™ by Given Imaging Ltd. Other sleeve dimensions may be used. According to other embodiments, sleeve 10 may be inserted into a housing of other in-vivo devices.

Figure 2A:
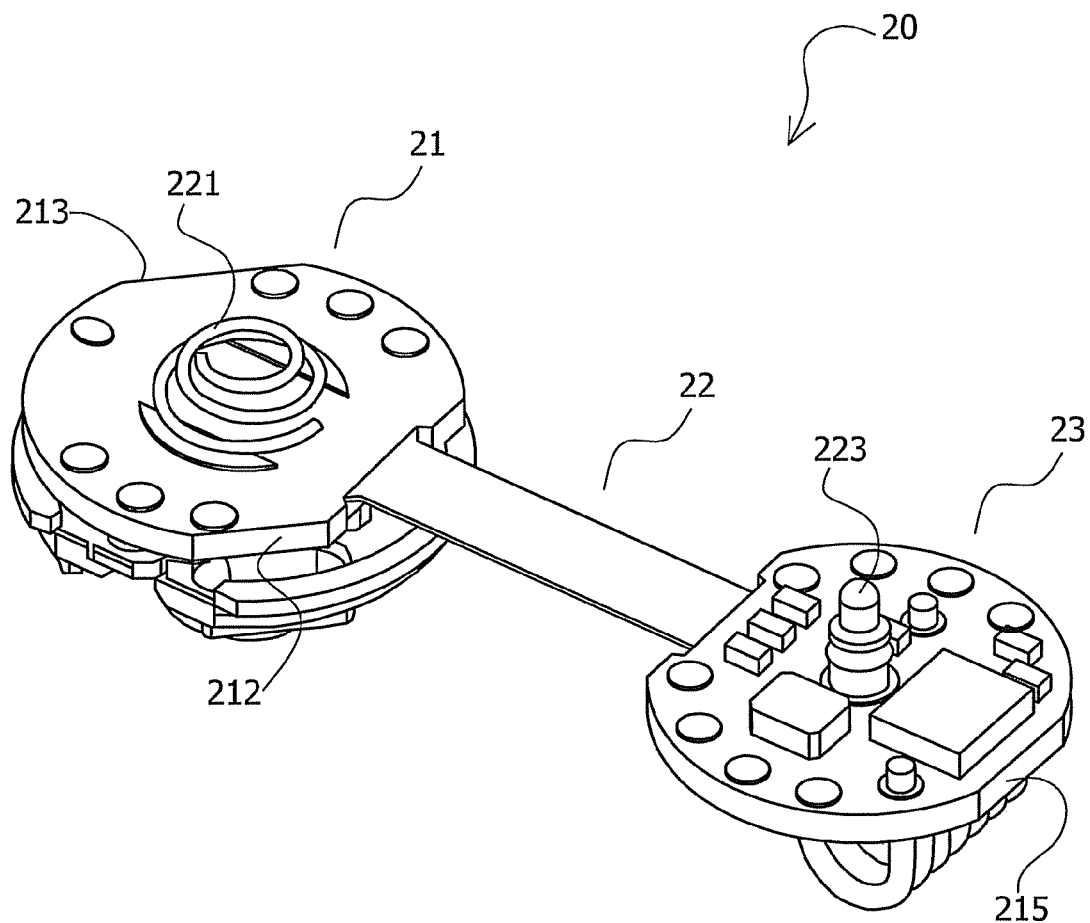
FIGS. 2A-D are schematic illustrations of an assembly process in accordance with one embodiment of the invention.

Reference is now made to FIGS. 2A-2D, which are schematic illustrations of an assembly process in accordance with one embodiment of the invention. In some embodiments, the assembly process comprises folding and insertion of a rigid-flex PCB into a sleeve which may subsequently be inserted into a swallowable endoscopy capsule. According to an embodiment of the invention, as depicted in FIG. 2A, there is provided a rigid-flex circuit board 20. In some embodiments, circuit board 20 may comprise a first rigid portion 21, a second rigid portion 23 and a flexible portion 22 connecting the two rigid portions one to the other. In other embodiments, there may be more than two rigid portions which may be connected in series by respective flexible portions.

The first rigid portion 21 may have mounted thereon an imager, at least one illumination source and an optical system which may comprise lenses. These components may be mounted on one side of the first rigid portion 21 of the PCB (not shown). Other components may be mounted on the first rigid portion 21. On the other side of the first rigid portion 21, there may be a battery contact (shown as a spring 221).

Figure 2B:
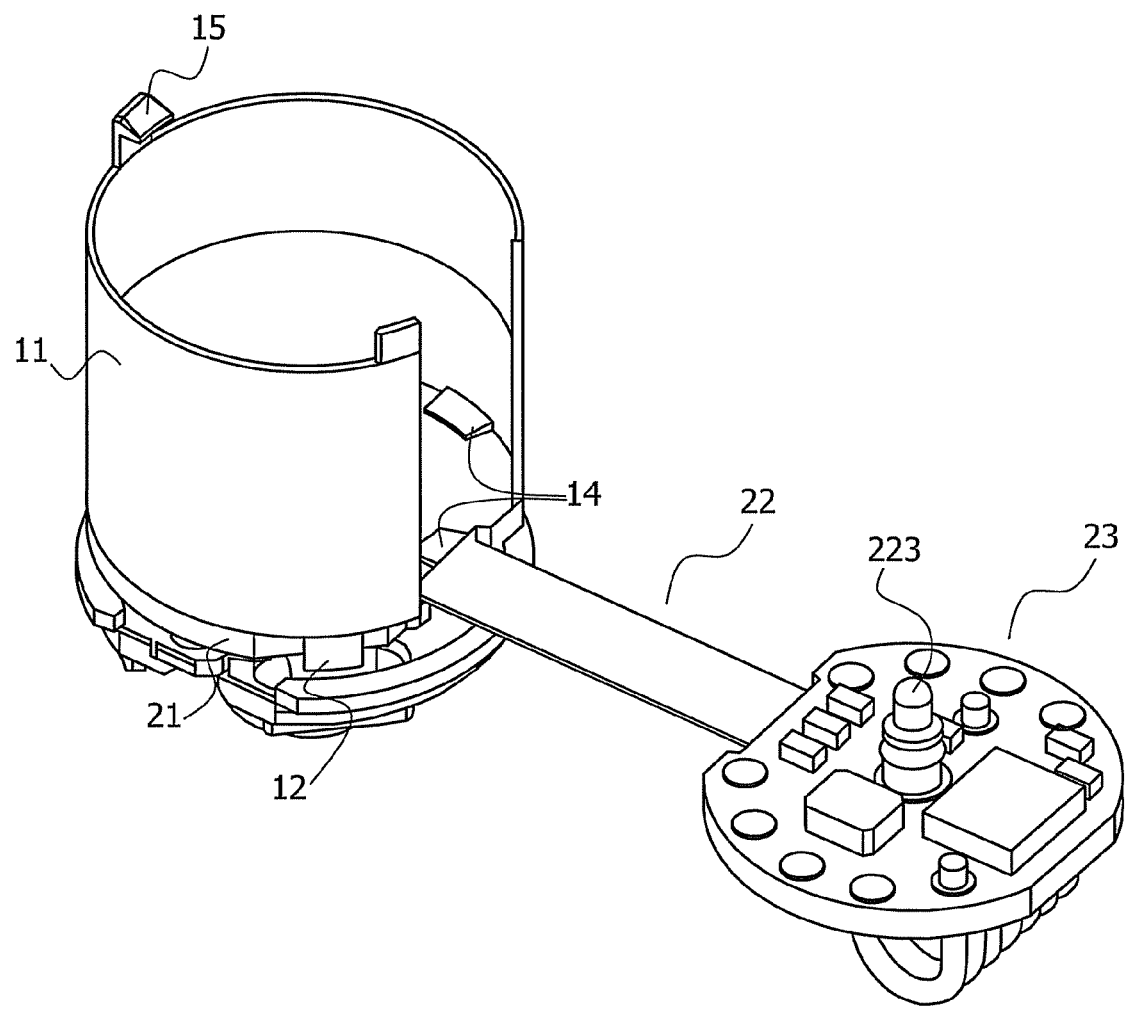
Figure 2C:
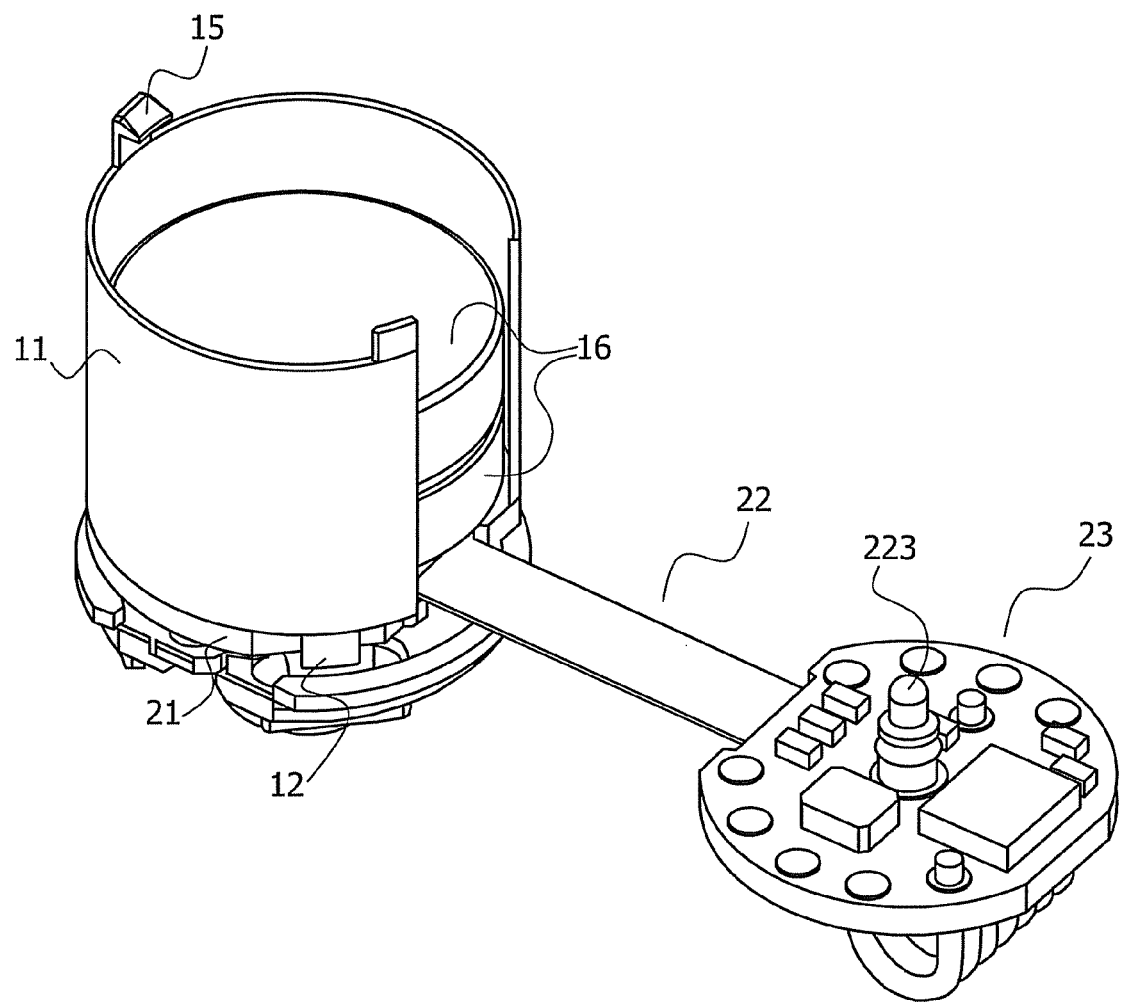
Figure 2D:
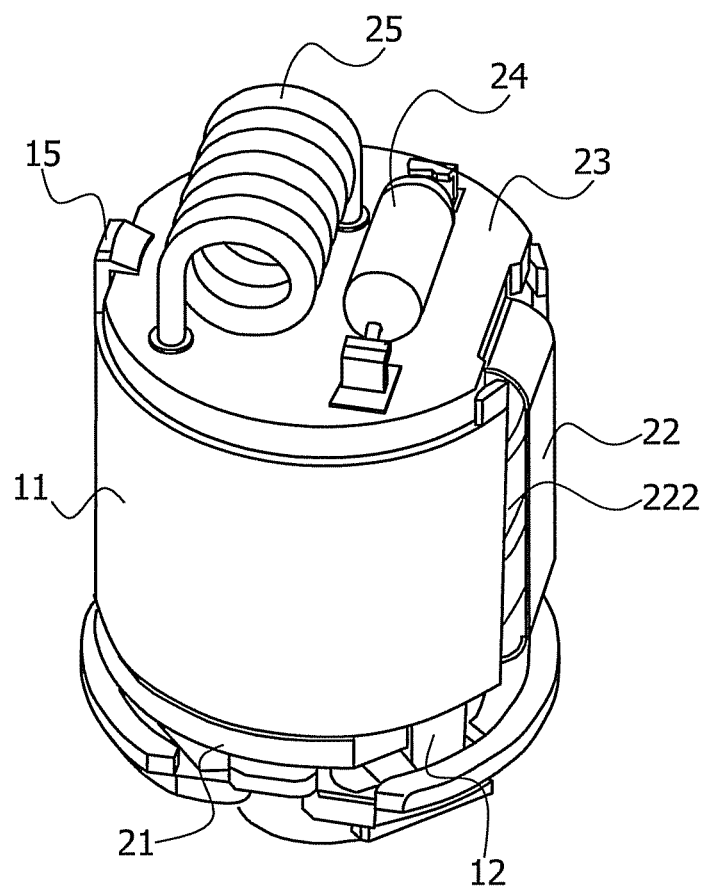

The second rigid portion 23 may have mounted thereon, on one side, a transmitter 24 and an antenna 25 (shown in FIG. 2D). Other components may be mounted on the second rigid portion 23. On the other side of second rigid portion 23, there may be, among other electronic components, a battery contact 223, such that when circuit board 20 is in a folded position, one or more batteries may be placed in between the first rigid portion 21 and the second rigid portion 23 in order to power components mounted on circuit board 20. The one or more batteries may be in contact with battery contacts from both sides, i.e., one battery contact from rigid portion 21 and another battery contact from rigid portion 23.

In one embodiment, the rigid portion 21 is not a perfect circle, but is instead truncated in those areas where rigid portion 21 is supposed to be inserted into grippers 12 and/or 13. In particular, in some embodiments, an arcuate portion of the circular shape of the rigid portion 21 is cut off, specifically in the areas where it would be snapped into grippers 12 and/or 13 when attached to an end of sleeve body 11, i.e., at areas 212 and/or 213 of rigid portion 21, respectively. These cut off portions 212,213 ensure better hold of the rigid portion 21 within the grippers 12 and/or 13, since more of the surface area of the rigid portion 21 (212 and/or 213) is overlapping the surface area of grippers 12 and/or 13.

Similarly, in some embodiments, an arcuate portion of the circular shape of the rigid portion 23 is cut off, specifically in the area where it would be snapped into gripper 15 when attached to an end of sleeve body 11, i.e., at area 215. For the same reason as before, truncating the rigid portion 23 in the areas where it would be snapped into gripper 15 ensures better hold of the rigid portion 23 within the gripper 15, since more of the surface area of the rigid portion 23 (215) is overlapping the surface area of gripper 15.

According to an embodiment of the invention, as depicted in FIG. 2B, rigid portion 21 is snapped into a first end of sleeve body 11. Rigid portion 21 is snapped into gripper 12 and/or gripper 13 (not shown). The first end of sleeve body 11 may comprise leaf springs 14 in addition to gripper 12 and/or gripper 13. According to an embodiment of the invention, rigid portion 21 may be snapped into gripper 12 and/or 13 such that it is held between gripper(s) 12 (and 13) and leaf springs 14. Typically, there are more than one gripper 12 and 13, and there are more than one leaf springs 14 holding or pushing the rigid portion 21 against grippers 12 and/or 13. The number of gripper 12 and 13 and leaf springs 14 may depend on the diameter of the rigid portion of the PCB. For example, the larger the diameter of the rigid portion, the more grippers and leaf springs there are for properly supporting the rigid portion. In other embodiments, the number of leaf springs may be the same for different sizes of the rigid portion; however, the leaf springs may have larger dimensions in order to provide adequate support.

According to an embodiment of the invention, as depicted in FIG. 2C, at least one battery 16 is inserted into sleeve body 11, after the first rigid portion 21 is snapped into grippers 12 and/or 13. In this embodiment, the diameter of battery 16 is slightly less than the diameter of sleeve 11 so as to provide for as little movement of battery 16 as possible within sleeve 11 when enclosed therein. In the embodiment shown in FIG. 2C, batteries 16 may be button-type or disk-shaped and may be stacked one atop another.

As shown in FIG. 2D, after the at least one battery 16 is inserted into sleeve body 11, the flexible portion 22 of rigid-flex circuit board 20 is folded and extended between the two ends 18 and 19 of the sleeve body 11. In some embodiments, the second rigid portion 23 is then snapped into gripper 15 such that rigid-flex circuit board 20 acquires its folded position. In some embodiments, there may be leaf springs on both ends of sleeve body 11, i.e., there may be leaf springs at the same end of sleeve body 11 where gripper 15 is, but opposite to the gripper 15. In these embodiments, the leaf springs may provide additional support to the second rigid portion 23 besides the support provided by gripper 15. The additional leaf springs may secure and firmly hold the second rigid portion 23 in between the gripper 15 and the leaf springs.

However, in other embodiments, there are no leaf springs 14 in addition to gripper 15, since the deformed, i.e., folded, flexible portion 22 of the rigid-flex PCB performs the functions of leaf spring 14. In this embodiment, flexible portion 22 has been folded from its original flat configuration, as in FIG. 2A, and pushes itself back against gripper 15. The flexible portion 22 of the PCB "wants" to return to its initial open configuration instead of the "un-natural" folded configuration, and provides the force against the underside of the overhanging portion of gripper 15, so there is no need for extra leaf springs to push the rigid portion 23 against gripper 15.

In some embodiments, the height of the sleeve 11 may be determined by the quantity and dimensions of the batteries 16 that are to be inserted into the sleeve body 11. The height of sleeve 11 may be specifically determined by the number and thickness of batteries 16. Accordingly, the battery/batteries 16 may push the second rigid portion 23 against gripper 15, in addition to the self pushing of the rigid-flex PCB flexible portion 22, while trying to return to its initial flat, i.e., unfolded, configuration.

In some embodiments, there is an opening 222 in the sleeve body 11 for flexible portion 22 to pass through. Since flexible portion 22 is folded near its connections to rigid portion 21 and rigid portion 23 (during assembly and folding of the rigid-flex PCB 20 into the sleeve 10), the flexible portion 22 needs some extra space for the folds. In order to keep the folds from being pressed within the sleeve body 11, flexible portion 22 is passed along an opening 222 that extends longitudinally in the sleeve body 11 between the two open ends of sleeve 10, i.e., from one end 18 of sleeve 11 to the other end 19. In some embodiments, there is also provided a space between the sleeve body 11 and the housing it is inserted into such that the flexible portion 22 is not pressed against the housing and so that the folds of flexible portion 22 would not be damaged. In other embodiments, the sleeve body 11 may not have an opening but instead may have a larger diameter to include the space needed to keep the folds of the flexible portion 22 unharmed. In these embodiments, in order to properly hold the rigid portions 21 and 23 within the grippers of the sleeve 10, either the diameter of the rigid portions 21 and 23 is larger and/or the configuration of the grippers is designed to fit the larger diameter of sleeve 10.

In some embodiments, rigid portion 23 may have mounted thereon a transmitter 24 and an antenna 25, preferably on the side of rigid portion 23 which is external to the sleeve body 11. In some embodiments, transmitter 24 and antenna 25 may be mounted on rigid portion 23 subsequent to insertion of rigid portion 23 into gripper 15. Other components may be electrically connected to rigid portion 23.

Figure 3:
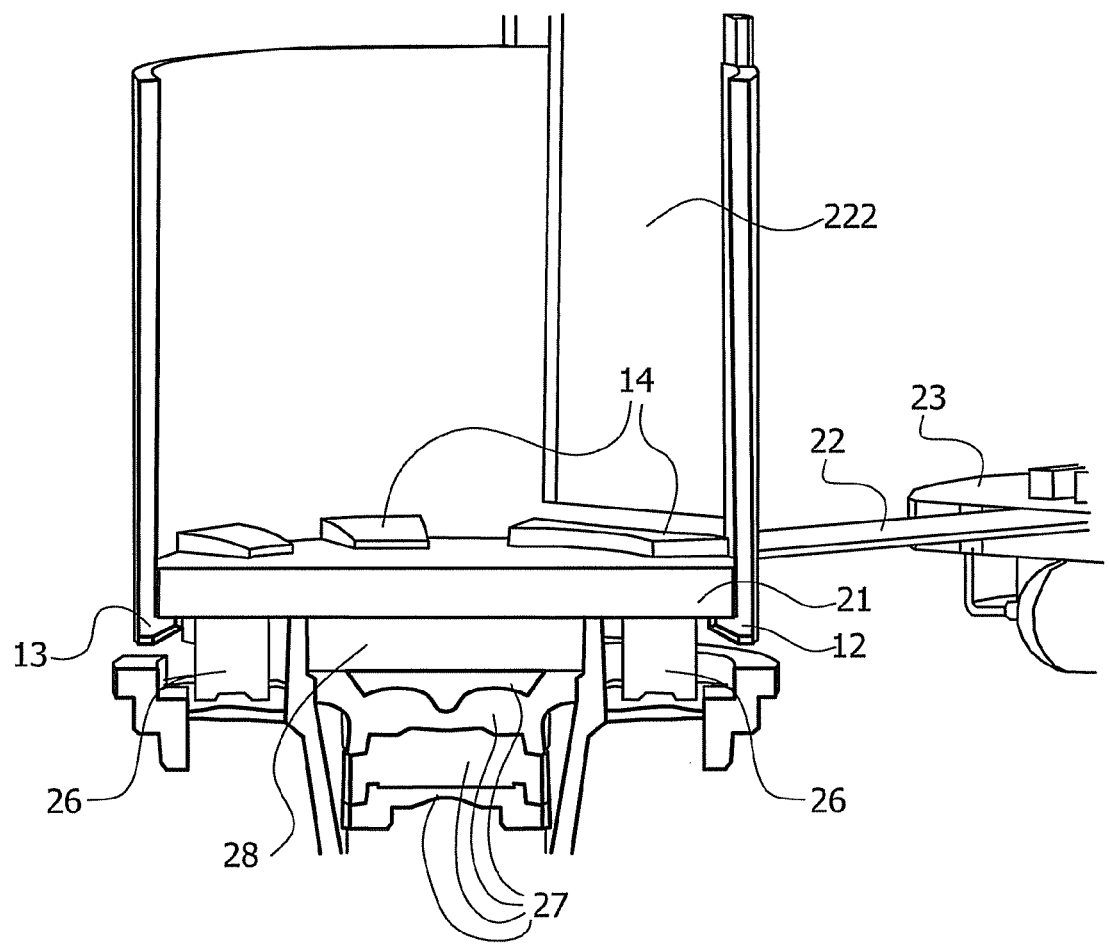
FIG. 3 is a schematic illustration of a vertical cross section of a sleeve for folding a rigid-flex PCB in accordance with one embodiment of the invention.

Reference is now made to FIG. 3 which is a schematic illustration of a vertical cross section of a sleeve for folding a rigid-flex PCB in accordance with one embodiment of the invention. In this vertical cross section, the rigid portion 21 is held between grippers 12 and 13 on its outer side and leaf springs 14 on its inner side. Leaf springs 14 are shown to provide additional support for the rigid portion 21 of the rigid-flex PCB.

In some embodiments, rigid portion 21, supported by leaf springs 14, may have mounted thereon illumination sources 26, image sensor 28 and an optical system 27 placed on top of the imager 28. In some embodiments, the optical system 27 may comprise one lens, but in other embodiments optical system 27 may comprise more than one lens. According to some embodiments, leaf springs 14 may apply an axial force on the rigid portion 21 such that the rigid portion 21 is pushed against grippers 12 and 13. This ensures a tight hold of the rigid portion 21 between the grippers 12 (and/or 13) and leaf springs 14, and further ensures that rigid-flex PCB 20 is held in a folded configuration before it is inserted into an in-vivo device.

Figure 4:
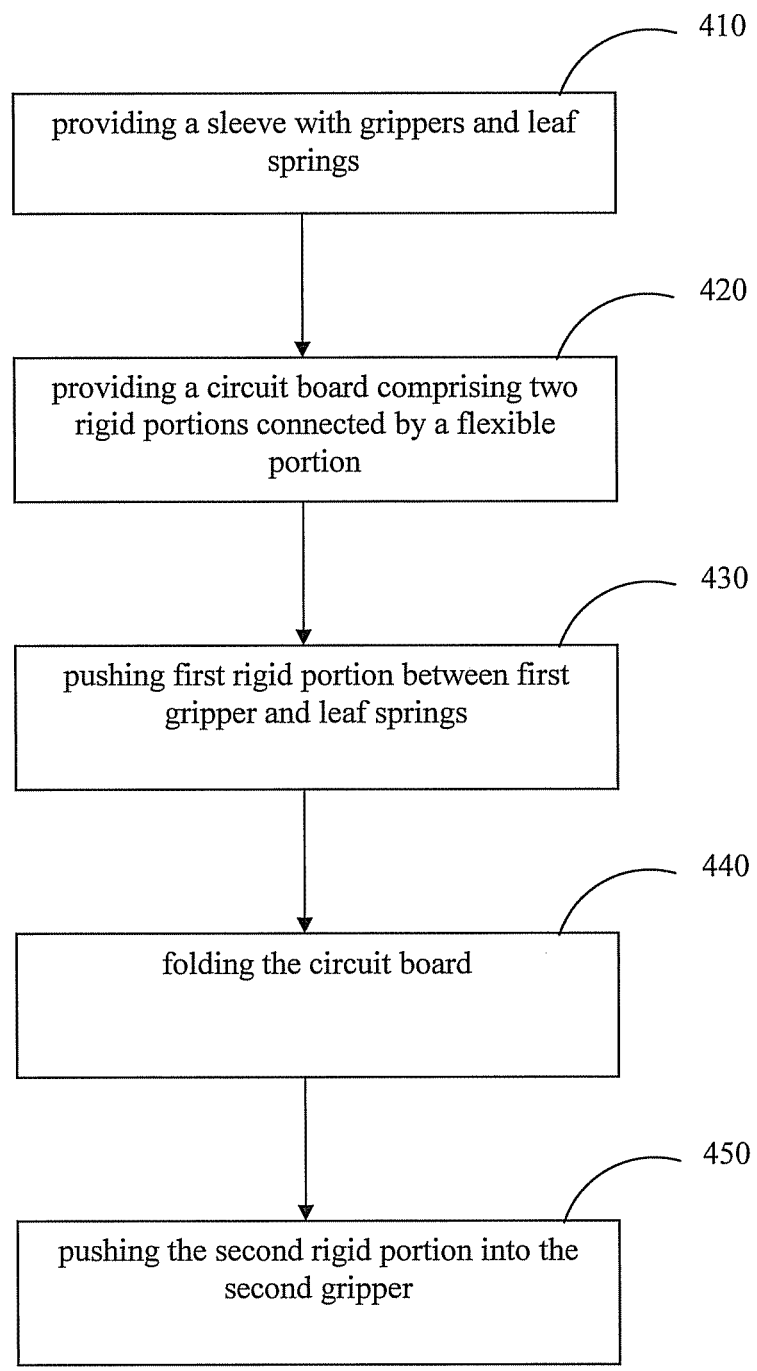
FIG. 4 is a flow-chart illustrating a method of assembly in accordance with one embodiment of the invention.

Reference is now made to FIG. 4, which is a flow-chart illustrating a method of assembly in accordance with one embodiments of the invention. According to an embodiment of the invention, a method of assembly may comprise providing a sleeve with two open ends (block 410). According to some embodiments, the sleeve provided may be sleeve 10 as illustrated in FIG. 1. However, in other embodiments, the sleeve may have other configurations and/or dimensions. In some embodiments, as for example in sleeve 10, a first end of the sleeve may comprise a first gripper and at least two leaf springs, while the second sleeve's end may comprise a second gripper. In some embodiments, the second sleeve's end may also comprise leaf springs as does the first sleeve's end.

According to an embodiment of the invention, the method may comprise providing a circuit board (block 420). In some embodiments, the circuit board may be a rigid-flex PCB which may comprise a first rigid portion and a second rigid portion which are connected by a flexible portion. The method may comprise pushing the first rigid portion of the circuit board into the first gripper (block 430). In some embodiments, the sleeve may comprise at least two leaf springs on the same first sleeve's end but opposite to the gripper. The first rigid portion of the PCB may be pushed into the first gripper such that the rigid portion is held between the first gripper and the leaf springs. The leaf springs may provide support for the first rigid portion and moreover may push the rigid portion against the gripper so that the first rigid portion is tightly held within the sleeve's first end.

In some embodiments, the method comprises folding the PCB while passing the flexible portion, which connects between the first and second rigid portions, between the first and second sleeve's ends (block 440). In order to achieve a final folded configuration of the rigid-flex PCB, the method may further comprise pushing the second rigid portion into the second gripper (block 450). In some embodiments, the second sleeve's end may comprise leaf springs in addition to the second gripper, but in other embodiments, there may be only a gripper.

In some embodiments, the method may comprise placing at least one battery into the sleeve subsequent to pushing/snapping said first rigid portion into the first gripper and prior to folding the circuit board. The number and size of batteries which are intended to be inserted into the sleeve for powering the electronic components mounted on the PCB, would determine the dimensions of the sleeve, namely its width and height.

In some embodiments, there may be a plurality of rigid portions and a plurality of flexible portions, typically alternately, which may be folded into a sleeve. In these embodiments, the first rigid portion and the second rigid portion may be positioned at each end of the rigid-flex PCB, and may be inserted into the grippers and/or in between the grippers and leaf springs. In some embodiments, the plurality of flexible and rigid portions in between the rigid portions on each end of the PCB may be preferably folded in a stacked configuration. According to some embodiments, the dimensions of the sleeve may be determined by the length and diameter of the plurality of rigid and flexible portions of the PCB, along with the dimensions of the batteries to be placed in between the PCB portions.

According to some embodiments, the assembly process may comprise inserting the sleeve into an in-vivo device's housing. The in-vivo device may pass through a patient's body, for example, through the gastrointestinal (GI) tract. An in-vivo device may be an endoscopy capsule and its housing may be the capsule's case. After the sleeve, for example sleeve 10, is inserted into an endoscopy capsule's housing, an optical dome may be placed over one end of the in-vivo device's housing. The end of the housing where the dome may be placed is typically at a side of the PCB where an imager is mounted. The transparent dome may be placed over an imager and an optical system to protect the imager and optical system during the time that they are operated to acquire in-vivo images through the dome. In addition, the outer surface of the dome functions to push tissue away from the imager when passing through ducts with collapsing walls, for example, the small intestine. Pushing the tissue away from the imager may allow image acquisition of tissue close by the capsule.

In some embodiments, a cover may be placed over the other open end of the housing, opposite to the optical dome. In some embodiments, the cover may be opaque. However, in other embodiments, the cover opposite the dome may be transparent. Furthermore, the cover may be another optical dome, specifically if another imager is mounted on the PCB on the side of the second rigid portion.

Sleeve body 11, for example, may serve as a barrier between the endoscopy capsule's housing and the batteries which are inserted into the housing. If one of the circuits in the endoscopy capsule is short circuited, as can happen to any electrical circuit, the batteries may over-heat. If the batteries are in contact with the capsule's housing, the housing of the endoscopy capsule would also heat, which may cause damage to tissue in contact with the housing. In order to prevent such an event, the sleeve creates a distance between the batteries and the capsule's housing and so prevents over-heating of the housing and of the tissue surrounding it.

In some embodiments, in order to prevent over-heating of a tissue which may be in contact with the device's housing in adverse events of short circuits where the batteries over-heat, a sleeve for covering the batteries may be inserted into the housing. The sleeve, for example, sleeve body 11 as shown in FIG. 2C, may create a distance between the batteries 16 within the sleeve 11 and the housing of the device into which sleeve 11 is inserted. In other embodiments, there may be other mechanisms creating distance between the batteries and the housing of the device they are inserted into.

Figure 5:
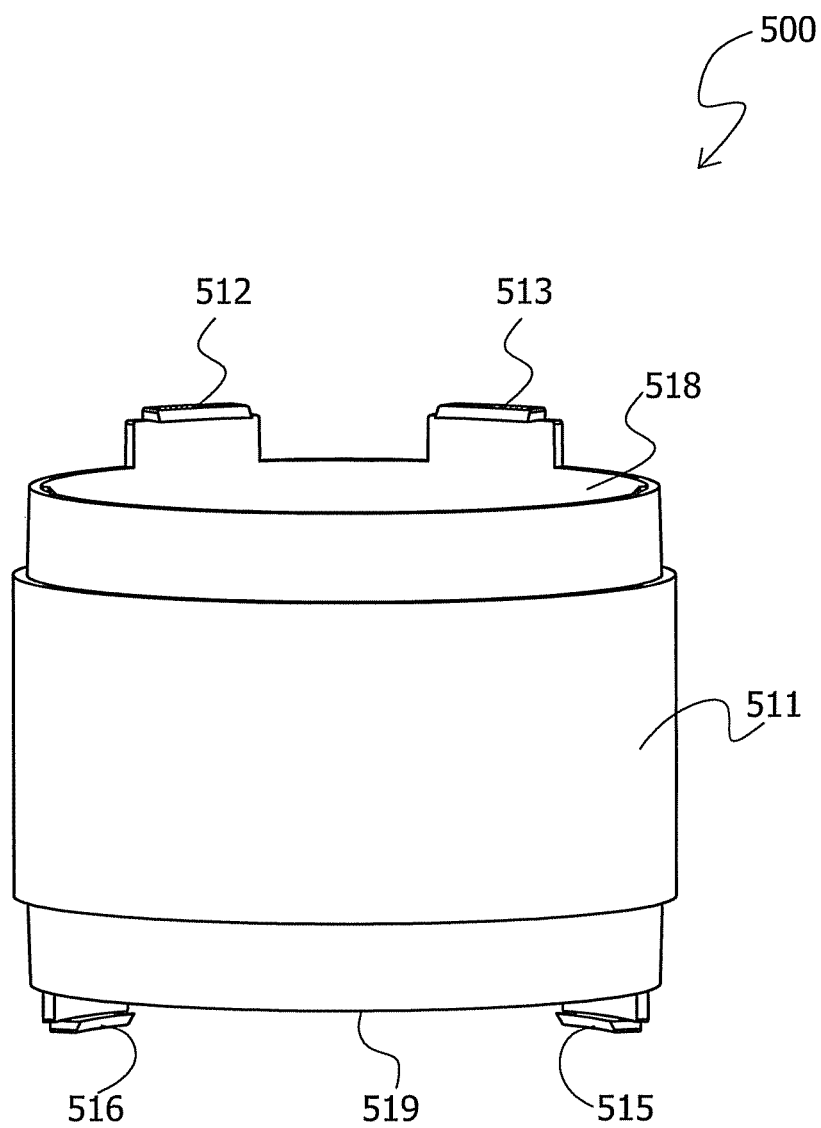
FIG. 5 is a schematic illustration of a side view of an in-vivo device's housing in accordance with one embodiment of the invention.

Reference is now made to FIG. 5, which is a schematic illustration of a side view of an in-vivo device's housing 500 in accordance with one embodiment of the invention. According to an embodiment of the invention, as depicted in FIG. 5, there is provided an in-vivo device's housing 500 into which a rigid-flex PCB is inserted, i.e., without use of a separate sleeve 10, as shown in FIGS. 1-4. The device's housing 500 comprises a housing body 511 and two open ends 518 and 519. Housing body 511 may be cylindrical, as shown in FIG. 5, but may also have other shapes that can conveniently and efficiently form an in-vivo device. In preferred embodiments, housing body 511 is open at both ends. In some embodiments, there may be at least one gripper 512 on one open end 518 of the housing body 511 and at least one gripper 515 on the other open end 519 of the housing body 511. In some embodiments, there may be one or more additional grippers on either end, such as grippers 513 and 516. Gripper 512 and/or gripper 513 are for retaining a rigid portion of a rigid-flex PCB perpendicularly to the axial direction of the housing 511, against the upper rim of the housing 511. Gripper 515 and/or gripper 516 are to retain a rigid portion of the rigid-flex PCB perpendicularly to the axial direction of the housing 511 against the lower rim of the housing 511.

Figure 6:
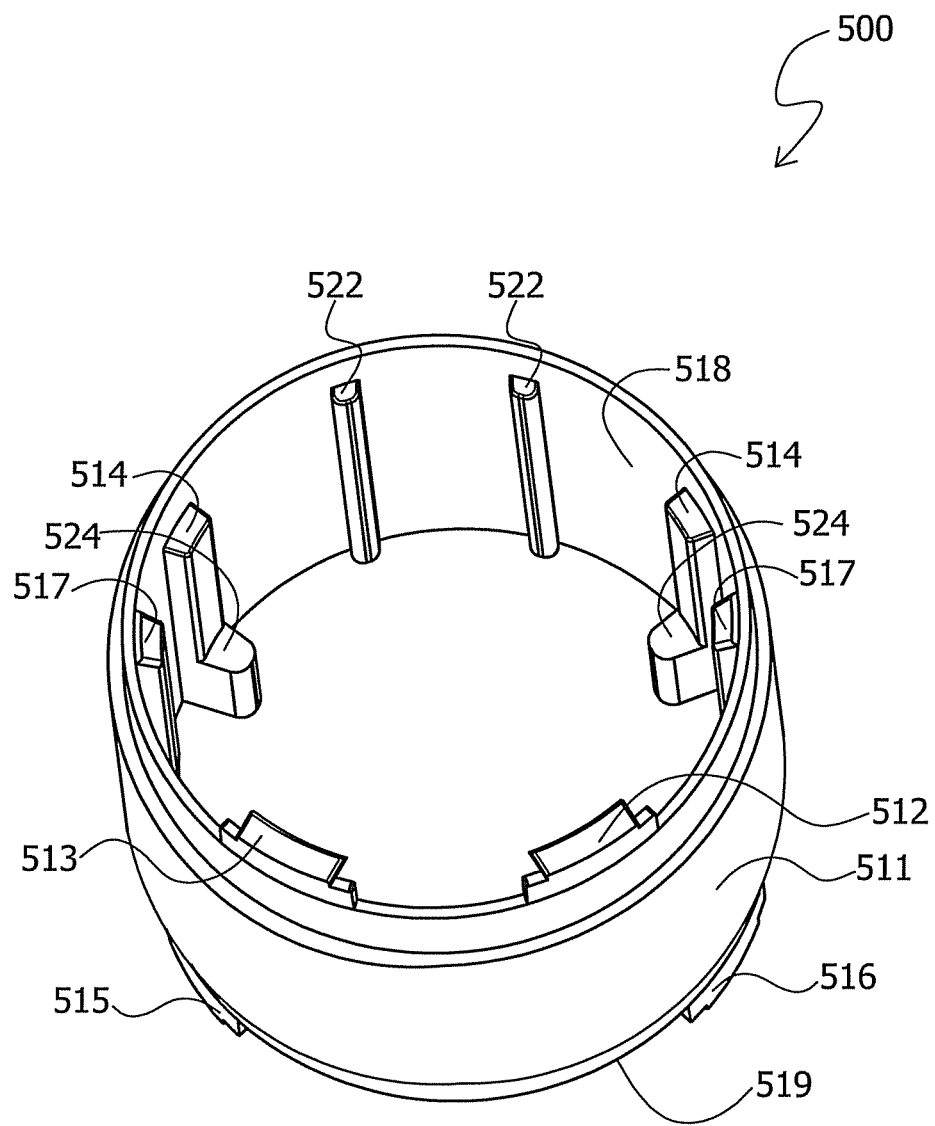
FIG. 6 is a schematic illustration of an upper view of an in-vivo device's housing in accordance with one embodiment of the invention.

Reference is now made to FIG. 6 which is a schematic illustration of an upper view of an in-vivo device's housing 500 in accordance with one embodiment of the invention.

According to some embodiments, as depicted in FIG. 6, housing 500 may further comprise ribs 514 and 517 extending longitudinally along, and protruding inward from, the inner side of housing body 511. In some embodiments, some of ribs, e.g., ribs 514 may comprise at one end thereof a projection 524 that projects farther inward than do ribs 514. Projection 524 may serve as a base to support the batteries that have been inserted into the housing 511 for powering the electrical components mounted on the rigid-flex PCB which may be folded in the housing body 511. According to an embodiment of the invention, bottom grippers 515 and 516 retain a rigid portion of the rigid-flex PCB perpendicularly to the axial direction of the housing 511, and batteries may then be inserted into housing 511 from the upper side 518 of housing 511, for powering the electrical components mounted on that retained rigid portion. Projection 524 supports the batteries and further assists the batteries to maintain a position parallel to the rigid portion of the rigid-flex PCB so as to confirm adequate electrical contact between the surface of the batteries and the electrical components on the rigid portion. Following insertion of the batteries, upper grippers 512 and 513 retain a second rigid portion of the rigid-flex PCB perpendicularly to the axial direction of the housing 511.

According to some embodiments, ribs 514, 517 may space the batteries away from housing 511 and prevent direct contact between the two. Ribs 514, 517 may create a distance between the batteries and the housing 511 such that in a case of a short circuit, for example, housing 511 would not overheat as a result of the over-heating of the batteries. If the batteries would over-heat as a result of a short circuit in one or more of the electrical circuits of the rigid-flex PCB, the heat would distribute from the batteries to the ribs 514, 517 and only then to the housing 511, and the spacing between the batteries and the housing 511 created by ribs 514, 517 helps to allow the batteries to cool off. Since there is no direct contact between the batteries and the housing 511, the heat intensity is reduced before being transferred to the housing 511, such that undesirable heating would be caused to the tissue in contact with the in-vivo device.

In some embodiments, housing 511 may further comprise ribs 522 between which the flexible portion of the rigid-flex PCB is positioned. The flexible portion of the rigid-flex circuit board is folded and extended between ribs 522 and further between the two ends 518 and 519 of the housing body 511. In some embodiments, ribs 522 function as a groove for the flexible portion to pass along so that the flexible portion is held in place and wouldn't move within housing 511. In addition, ribs 522 assist in creating a distance between the batteries and the housing 511, such as ribs 514 and 517, in an event of the batteries over-heating.

It will be appreciated that the present invention is not limited to what has been particularly shown and described hereinabove. Rather the scope of the present invention is defined only by the claims which follow.

What is claimed is:

1. A sleeve and circuit board configuration for insertion into a swallowable capsule housing of an in vivo sensing device, wherein said sleeve is configured for holding said circuit board in a folded configuration, said sleeve being a single structure having a cylindrical shape and comprising:
   a first end located at a first terminal end of the sleeve and comprising a first gripper and at least one leaf spring;
   a second end located at a second terminal end of the sleeve opposing the first terminal end and comprising a second gripper;
   a slit through said sleeve extending longitudinally along a longitudinal axis of said cylindrically shaped sleeve from said first end to said second end; and
   a circuit board comprising a first rigid portion, a second rigid portion and a flexible portion connecting the first rigid portion and the second rigid portion;
   wherein the first gripper and the at least one leaf spring hold the first rigid portion of said circuit board between the first gripper and the at least one leaf spring on the first end, the second gripper holds the second rigid portion of the circuit board on the second end, wherein the flexible portion of the circuit board from the first rigid portion to the second rigid portion extends along the slit and along a longitudinal plane of the sleeve, and wherein each of the first and second rigid portions lie in a radial plane at the first and second terminal ends of the sleeve, respectively.

2. The sleeve and circuit board configuration according to claim 1 further comprising space for inserting at least one battery between said first and second rigid portions.

3. The sleeve and circuit board configuration according to claim 1, wherein said sleeve is manufactured from a material selected from a group consisting of:
   Acetal, ABS, Polycarbonate, and Polyimide.

4. A method of assembling a swallowable in vivo device, the method comprising:
   providing a sleeve with two open ends and a slit extending longitudinally through a side wall of the sleeve, wherein a first sleeve end comprises a first gripper and at least one leaf spring, and wherein a second sleeve end comprises a second gripper;
   providing a circuit board having a first rigid portion and a second rigid portion connected by a flexible portion;
   pushing said first rigid portion into the first gripper, such that said first rigid portion is placed between, and held by, the first gripper and the at least one leaf spring;
   folding the circuit board while passing the flexible portion within said slit between the first and second sleeve ends;
   pushing the second rigid portion into the second gripper; and
   inserting said sleeve into a swallowable housing.

5. The method according to claim 4 further comprising the step of inserting at least one battery into the sleeve prior to folding the circuit board.

6. The method according to claim 4 further comprising the steps of:
   placing an optical dome on one side of the in-vivo device's housing; and
   placing a cover on another side of the in-vivo device's housing.

7. The method according to claim 6, wherein said cover is an optical dome.

8. The method according to claim 6, wherein said in-vivo device is a swallowable capsule.

9. The method according to claim 4, wherein said sleeve comprises an in-vivo device's housing, further comprising the steps of:
   placing an optical dome on one side of the sleeve; and
   placing a cover on another side of the sleeve.

10. The sleeve and circuit board configuration according to claim 1, wherein each of said first and second rigid portions have first and second opposing faces, such that said first gripper contacts the first opposing face of the first rigid portion and said at least one leaf spring contacts the second opposing face of the first rigid portion, and wherein the second gripper holds the second rigid portion.

11. The sleeve and circuit board configuration according to claim 10, wherein said first and second grippers further comprise an overhanging portion extending radially inward toward the axial center of said sleeve.

12. The sleeve and circuit board configuration according to claim 11, wherein the at least one leaf spring applies a force to said second opposing face of said first rigid portion, pushing said first rigid portion toward an underside of the overhanging portion of said first gripper.

13. The sleeve and circuit board configuration according to claim 12, wherein the force is an axial force pushing toward said underside of the overhanging portion of said first gripper.

14. The sleeve and circuit board configuration according to claim 1, wherein said at least one leaf spring has a planar shape and extends radially inward toward an axial center of said sleeve.

15. The sleeve and circuit board configuration according to claim 1, wherein said at least one leaf spring comprises at least two leaf springs.

16. The method according to claim 4,
   wherein each of said first and second rigid portions of said circuit board have first and second opposing faces; and
   wherein said step of pushing further comprises pushing said first rigid portion into the first gripper, such that said first rigid portion is placed between, and held by, the first gripper on said first opposing face of the first rigid portion and the at least one leaf spring on said second opposing face of the first rigid portion.

17. The method according to claim 16, wherein said first and second grippers further comprise an overhanging portion extending radially inward toward the axial center of said sleeve.

18. The method according to claim 17, wherein the at least one leaf spring applies a force to said second opposing face of said first rigid portion, pushing said first rigid portion toward an underside of the overhanging portion of said first gripper.

19. The method according to claim 18, wherein the force is an axial force pushing toward said underside of the overhanging portion of said first gripper.

20. The method according to claim 4, wherein said at least one leaf spring has a planar shape and extends radially inward toward an axial center of said sleeve.

21. The method according to claim 4, wherein said at least one leaf spring comprises at least two leaf springs.

* * * * *